United States Patent
Falk

(10) Patent No.: US 8,530,601 B2
(45) Date of Patent: Sep. 10, 2013

(54) COPOLYMERS OF EPOXY COMPOUNDS AND AMINO SILANES

(75) Inventor: Benjamin Falk, Yorktown Heights, NY (US)

(73) Assignee: Momentive Performance Materials Inc., Waterford, NY (US)

( * ) Notice: Subject to any disclaimer, the term of this patent is extended or adjusted under 35 U.S.C. 154(b) by 204 days.

(21) Appl. No.: 12/741,063

(22) PCT Filed: Oct. 31, 2008

(86) PCT No.: PCT/US2008/012365
§ 371 (c)(1),
(2), (4) Date: Aug. 24, 2010

(87) PCT Pub. No.: WO2009/061371
PCT Pub. Date: May 14, 2009

(65) Prior Publication Data
US 2011/0021096 A1    Jan. 27, 2011

Related U.S. Application Data

(63) Continuation of application No. 12/050,543, filed on Mar. 18, 2008.

(60) Provisional application No. 60/984,753, filed on Nov. 2, 2007.

(51) Int. Cl.
*C08G 77/26* (2006.01)

(52) U.S. Cl.
USPC .......................................................... 528/34

(58) Field of Classification Search
USPC .......................................... 528/34; 525/477
See application file for complete search history.

(56) References Cited

U.S. PATENT DOCUMENTS

| 4,972,008 A |   | 11/1990 | Lee et al. |   |
|---|---|---|---|---|
| 5,384,340 A |   | 1/1995 | Hara et al. |   |
| 6,075,110 A | * | 6/2000 | Mohri et al. | 528/14 |

FOREIGN PATENT DOCUMENTS

| CA | 866244 |   | 3/1971 |
|---|---|---|---|
| EP | 1 116 813 | * | 7/2001 |
| JP | 54-129098 |   | 10/1979 |
| JP | 05-214216 |   | 8/1993 |
| JP | 05-331417 |   | 12/1993 |
| JP | 06-080946 |   | 3/1994 |
| JP | 06 287483 | * | 10/1994 |
| JP | 07-258503 |   | 10/1995 |
| JP | 2005-281528 |   | 10/2005 |
| KR | 2005-0088650 |   | 9/2005 |
| WO | 80/00847 |   | 5/1980 |
| WO | 91/06588 |   | 5/1991 |
| WO | 2007/149537 |   | 12/2007 |

OTHER PUBLICATIONS

JP 06 287483 Machine translation.*
Japanese Office Action for Patent Application No. 2010-533,077, dated Mar. 19, 2013.

* cited by examiner

*Primary Examiner* — Kuo-Liang Peng
(74) *Attorney, Agent, or Firm* — Dominick G. Vicari; Kenneth S. Wheelock

(57) ABSTRACT

The present invention provides for a composition comprising the reaction product of a. an oxirane or oxetane compound comprising at least two oxirane or oxetane groups; and b. an amino silane having the formula: $N(H)(R^1)R^2Si(OR^3)3\text{-}a\text{-}b\text{-}c(OR^4)a(R^5Si(OR^6)d(R^7)e)$ b Rc with $R^1$ is chosen from the group consisting of H or a monovalent hydrocarbon radical containing one to 20 carbon atoms; $R^2$ and $R^5$ are independently selected from a group consisting of oxygen or a divalent linear or branched hydrocarbon radical consisting of 1-60 carbons; $R^4$ is a hydrocarbon radical that contains 3 to 200 carbon atoms; $R^3$, $R^6$, $R^7$, and $R^8$ and are each independently selected from the group of monovalent linear or branched hydrocarbon radicals having from 1 to 200 carbon atoms; the subscript b is zero or a positive number and has a value ranging from 0 to 3; the subscripts a, and c are zero or positive and have a value ranging from 0 to 3 subject to the limitation that $(a+b+c) \leq 3$; the subscripts d and e are zero or positive and have a value ranging from 0 to 3 subject to the limitation that $(d+e) \leq 3$.

10 Claims, No Drawings

COPOLYMERS OF EPOXY COMPOUNDS AND AMINO SILANES

CROSS REFERENCE TO RELATED APPLICATIONS

This application is a national phase application of PCT/US2008/012365 filed Oct. 31, 2008, which is a continuation of U.S. application No. 12/050,543 filed Mar. 18, 2008, which claims priority to U.S. Provisional Application No. 60/984,753 filed Nov. 2, 2007.

FIELD OF THE INVENTION

The present invention relates to novel copolymers formed as the reaction product of epoxy compounds and amino silanes.

BACKGROUND OF THE INVENTION

U.S. Pat. No. 4,062,999 A describes a process for treating textile fibers with a mixture of an amino functional silane and an epoxy functional silicone. The unreacted mixture is applied to the fiber then heat treated in an oven.

U.S. Pat. No. 4,359,545 A describes the process of reacting an amino functional silicone and an epoxy functional silicone onto a textile surface. The blend is applied to a textile then heat-treated in an oven.

U.S. Pat. No. 5,384,340 describes the use of a moisture and or photo curable coatings system. The process involves first reacting an epoxy or methacryl functional silane with an excess of an amino functional silicone. The remaining unreacted amino groups are then reacted with an epoxy or isocyano functional vinyl containing molecule. The resulting material contains both moisture curable alkoxy silane groups and free radical curable vinyl groups.

EP 1,116,813 A1 describes a textile treatment composition containing siloxanes having epoxy- and glycol-functionalities and either an aminosilane or a silicone quaternary ammonium compound. The composition is preferably formulated as an aqueous emulsion. The emulsion is applied to the textile surface followed by heat treatment to cure the mixture.

U.S. Pat. No. 5,102,930 A describes a silicone-based fabric finishing agent that is suitable for finishing a fabric material containing keratinous fibers, e.g., wool. The fabric finishing agent is an aqueous emulsion of a hydroxy-containing organopolysiloxane with an admixture of a mixture of colloidal silica and a reaction product of an amino-functional alkoxy silane or a hydrolysis product thereof with an acid anhydride, an epoxy-functional alkoxy silane compound and a curing catalyst.

U.S. Pat. No. 6,475,568 B1 describes the synthesis of non-crosslinkable silicone polyether non-(AB)n materials that do not contain silane or reactive groups. Modified silicones can exhibit a variety of physical properties. The polymers can be modified to be hydrophilic, lipophilic and hydrophobic depending on the nature of the organic substituents. Recently, linear alternating copolymers and linear random copolymers have been made using alkyl or polyether, and polydimethylsiloxane units. These materials have shown utility in a variety of applications including personal care (hair conditioners, skin care and color cosmetics), textile treatments, hard surface modifiers, agricultural adjuncts, and the like. Unfortunately these materials are liquids and show limited durability when applied to a surface.

SUMMARY OF THE INVENTION

The present invention provides for a composition comprising the reaction product of
a) an oxirane or oxetane compound comprising at least two oxirane or oxetane groups; and
b) an amino silane having the formula:

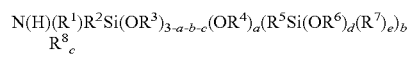

with $R^1$ is chosen from the group consisting of H or a monovalent hydrocarbon radical containing one to 20 carbon atoms;
$R^2$ is selected from a group consisting of a divalent linear or branched hydrocarbon radical consisting of 1-60 carbons;
$R^4$ is a hydrocarbon radical that contains 3 to 200 carbon atoms;
$R^5$ is selected from a group consisting of oxygen or a divalent linear or branched hydrocarbon radical consisting of 1-60 carbons;
$R^3$, $R^6$, $R^7$, and $R^8$ and are each independently selected from the group of monovalent linear or branched hydrocarbon radicals having from 1 to 200 carbon atoms;
the subscript b is zero or a positive number and has a value ranging from 0 to 3;
the subscripts a, and c are zero or positive and have a value ranging from 0 to 3 subject to the limitation that (a+b+c) $\leq 3$;
the subscripts d and e are zero or positive and have a value ranging from 0 to 3 subject to the limitation that (d+e) $\leq 3$.

DETAILED DESCRIPTION OF THE INVENTION

The present invention provides for a composition comprising the reaction product of
a) an oxirane or oxetane compound comprising at least two oxirane or oxetane groups; and
b) an amino silane having the formula:

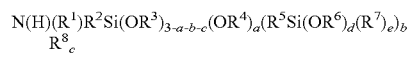

with $R^1$ is chosen from the group consisting of H or a monovalent hydrocarbon radical containing one to 20 carbon atoms;
$R^2$ is selected from a group consisting of a divalent linear or branched hydrocarbon radical consisting of 1-60 carbons;
$R^4$ is a hydrocarbon radical that contains 3 to 200 carbon atoms;
$R^5$ is selected from a group consisting of oxygen or a divalent linear or branched hydrocarbon radical consisting of 1-60 carbons;
$R^3$, $R^6$, $R^7$, and $R^8$ and are each independently selected from the group of monovalent linear or branched hydrocarbon radicals having from 1 to 200 carbon atoms;
the subscript b is zero or a positive number and has a value ranging from 0 to 3;
the subscripts a, and c are zero or positive and have a value ranging from 0 to 3 subject to the limitation that (a+b+c) $\leq 3$;
the subscripts d and e are zero or positive and have a value ranging from 0 to 3 subject to the limitation that (d+e) $\leq 3$;

The present invention further provides for such reaction product compositions where the oxirane or oxetane compound is selected from the group consisting of siloxanes, hydrocarbons and polyethers particularly where the oxirane or oxetane compound is a siloxane having the formula:

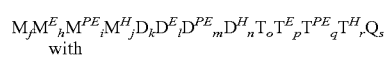

with
$M = R^9 R^{10} R^{11} SiO_{1/2}$;
$M^H = R^{12} R^{13} H\, SiO_{1/2}$;
$M^{PE} = R^{12} R^{13} (-CH_2 CH(R^{14})(R^{15}))_t O(R^{16})_u (C_2 H_4 O)_v (C_3 H_6 O)_w (C_4 H_8 O)_x R^{17}) SiO_{1/2}$;
$M^E = R^{12} R^{13} (R^E) SiO_{1/2}$
$D = R^{18} R^{19} SiO_{2/2}$; and
$D^H = R^{20} H SiO_{2/2}$ $D^{PE}=R^{20}(-CH_2CH(R^{14})(R^{15})_tO(R^{16})_u(C_2H_4O)_v(C_3H_6O)_w(C_4H_8O)_xR^{17})SiO_{2/2}$ $D^E=R^{20}R^ESiO_{2/2}$.

$T=R^{21}SiO_{3/2}$;

$T^H=HSiO_{3/2}$;

$T^{PE}=(-CH_2CH(R^{14})(R^{15})_tO(R^{16})_u(C_2H_4O)_v(C_3H_6O)_w(C_4H_8O)_xR^{17})SiO_{3/2}$;

$T^E=R^ESiO_{3/2}$; and $Q=SiO_{4/2}$;

where $R^9$, $R^{10}$, $R^{11}$, $R^{12}$, $R^{13}$, $R^{18}$, $R^{19}$, $R^{20}$, and $R^{21}$ are each independently selected from the group of monovalent hydrocarbon radicals having from 1 to 60 carbon atoms;

$R^{14}$ is H or a 1 to 6 carbon atom alkyl group; $R^{15}$ is a divalent alkyl radical of 1 to 6 carbons; $R^{16}$ is selected from the group of divalent radicals consisting of $-C_2H_4O-$, $-C_3H_6O-$, and $-C_4H_8O-$; $R^{17}$ is H, a monofunctional hydrocarbon radical of 1 to 6 carbons, or acetyl;

$R^E$ is independently a monovalent hydrocarbon radical containing one or more oxirane or oxetane moieties having from one to sixty carbon atoms;

the subscript f may be zero or positive subject to the limitation that when the subscript f is zero, h must be positive;

the subscript h may be zero or positive subject to the limitations that when h is zero, the subscript f must be positive, and that the sum of the subscripts h, l and p is positive;

the subscript k is zero or positive and has a value ranging from about 0 to about 1,000;

the subscript l is zero or positive and has a value ranging from about 0 to about 400 subject to the limitation that the sum of the subscripts h, l and p is positive;

the subscript o is zero or positive and has a value ranging from 0 to about 50;

the subscript p is zero or positive and has a value ranging from 0 to about 30 subject to the limitation that the sum of the subscripts h, l and p is positive;

the subscript s is zero or positive and has a value ranging from 0 to about 20;

the subscript i is zero or positive and has a value ranging from 0 to about 20;

the subscript m is zero or positive and has a value ranging from 0 to about 200;

the subscript q is zero or positive and has a value ranging from 0 to about 30;

the subscript j is zero or positive and has a value ranging from 0 to about 2;

the subscript n is zero or positive and has a value ranging from 0 to about 20;

the subscript r is zero or positive and has a value ranging from 0 to about 30;

the subscript t is zero or one;

the subscript u is zero or one;

the subscript v is zero or positive and has a value ranging from 0 to about 100 subject to the limitation that $(v+w+x)>0$;

the subscript w is zero or positive and has a value ranging from 0 to about 100 subject to the limitation that $(v+w+x)>0$;

the subscript x is zero or positive and has a value ranging from 0 to about 100 subject to the limitation that $(v+w+x)>0$;

or alternatively where the oxirane or oxetane compound is a hydrocarbon having the formula:

$$R^{22}_y(R^{23})_z(R^{24}_\alpha)(R^{25})_\beta$$

where $R^{22}$ and $R^{25}$ are independently a monovalent hydrocarbon radical containing one or more oxirane or oxetane moieties having from 3 to 12 carbon atoms;

$R^{23}$ and $R^{24}$ are each selected from the group consisting of H or a linear or branched monovalent hydrocarbon radical of 1 to 200 carbons;

the subscripts y, z, $\alpha$, $\beta$ are zero or positive ranging from zero to four subject to the limitation that $(y+\beta)>2$ or alternatively where the oxirane or oxetane compound is a polyether having the formula:

$$R^{26}O(R^{27})_\gamma(C_2H_4O)_\delta(C_3H_6O)_\epsilon(C_4H_8O)_\zeta R^{28}$$

where $R^{26}$ and $R^{28}$ are independently a monovalent hydrocarbon radical containing one or more oxirane or oxetane moieties having from 3 to 12 carbon atoms;

$R^{27}$ is selected from the group of divalent radicals consisting of $-C_2H_4O-$, $-C_3H_6O-$, and $-C_4H_8O-$;

the subscript $\gamma$ is zero or 1;

the subscript $\delta$ is zero or positive and has a value ranging from 0 to about 100 subject to the limitation that $(\delta+\epsilon+\zeta)>0$;

the subscript $\epsilon$ is zero or positive and has a value ranging from 0 to about 100 subject to the limitation that $(\delta+\epsilon+\zeta)>0$;

the subscript $\zeta$ is zero or positive and has a value ranging from 0 to about 100 subject to the limitation that $(\delta+\epsilon+\zeta)>0$.

The present invention also provides for a reaction product of an epoxy compound and an amino silane further comprising the reaction product of a compound having the formula:

$$R^{29}(R^{30})_\kappa Si(OR^{31})_{3-\eta-\theta}(R^{32})_\eta(OR^{33})_\theta$$

where $R^{29}$ is a monovalent hydrocarbon radical containing one or more oxirane or oxetane moieties having from 3 to 12 carbon atoms;

$R^{30}$ is a divalent hydrocarbon radical consisting of 1-60 carbons and the subscript $\kappa$ has a value of zero or 1; $R^{31}$ and $R^{32}$ are independently selected from the group of monovalent linear or branched hydrocarbon radicals having from 1 to 60 carbon atoms;

the subscript $\eta$ is zero or positive and has a value ranging from 0 to 3;

the subscript $\theta$ is greater than 0 and less than or equal to 3, subject to the limitation that $3-\eta-\theta$ is greater than or equal to zero;

$R^{33}$ is a hydrocarbon radical that contains 3 to 200 carbon atoms.

As used herein the phrase hydrocarbon radical includes hydrocarbon radicals that may be optionally substituted with hetero-atoms particularly nitrogen, oxygen, and sulfur, and may optionally contain ring structures such as oxirane and oxetane groups.

Preferred Embodiments

In reacting the oxirane or oxetane compounds with amino bearing compounds, the mole ratio of oxirane or epoxy groups to amino groups is preferably about 1 to about 4, more preferably greater than about 1.1 and less than about 3.9, and most preferably greater than about 1.2 and less than about 3.8. $R^1$ is preferably a monovalent hydrocarbon radical of from 1 to about 10 carbon atoms or hydrogen, more preferably from 1 to about 5 carbon atoms or hydrogen, most preferably $R^1$ is H. $R^2$ is preferably a monovalent hydrocarbon radical of from 1 to about 10 carbon atoms more preferably 2 to about 8 carbon atoms, and most preferably 3 to about 5 carbon atoms. $R^4$ is preferably a monovalent hydrocarbon radical of from 3 to about 10 carbon atoms more preferable 3 to about 8 carbon atoms most preferable 3 to about 5 carbon atoms. $R^3$, $R^6$, $R^7$, and $R^8$ are each preferably a monovalent hydrocarbon radical of from 1 to about 20 carbon atoms more preferably 1 to about 15 carbon atoms, most preferably 2 to about 8 carbon atoms. Subscript a is in the range of from 0 to about 3, preferably from about 1 to about 3, more preferably from about 2 to about 3, most preferably from 0 to about 1. Subscript b is in the range of 0 to about 25, more preferably 0 to about 15 and most preferably 3. Subscript c is in the range 0 to about 3, more preferably 0 to about 2, most preferably 0 to about 1. $R^9$, $R^{10}$, $R^{11}$, $R^{12}$, $R^{13}$, $R^{18}$, $R^{19}$, $R^{20}$, and $R^{21}$ are each preferably a monovalent hydrocarbon radical of from 1 to about 4 carbon atoms, more preferably 1 to about 3 carbon atoms, and most preferably 1 carbon atom. The subscripts f, l, m, n, o p, q, r, s are each in the range of 0 to about 200, more preferably 0 to about 100, and most preferably 0 to about 50. The subscript k is in the range of 0 to about 500, more preferably 5 to about 250, and most preferably 5 to about 150. The subscripts v, w, and x are each in the range of 0 to about 50, more preferably 0 to about 35, and most preferably 0 to about 25. $R^{23}$ and $R^{24}$ are each preferably a monovalent hydrocarbon radical of from 5 to about 1000 carbon atoms, more preferably 10 to about 500, and most preferably 10 to about 300. The subscripts $\delta$, $\epsilon$, $\zeta$ are in the range of 0 to about 50 more preferably, 0 to about 30, and most preferably 0 to about 15. $R^{31}$ and $R^{32}$ are each preferably a monovalent hydrocarbon radical of from 1 to about 10 carbon atoms, more preferably 1 to about 8 carbon atoms, and most preferably 1 to about 4 carbon atoms. $R^{33}$ are each preferably a monovalent hydrocarbon radical of from 3 to about 100 carbon atoms, more preferably 3 to about 50 carbon atoms, most preferably 3 to about 10 carbon atoms.

Reference is made to substances, components, or ingredients in existence at the time just before first contacted, formed in situ, blended, or mixed with one or more other substances, components, or ingredients in accordance with the present disclosure. A substance, component or ingredient identified as a reaction product, resulting mixture, or the like may gain an identity, property, or character through a chemical reaction or transformation during the course of contacting, in situ formation, blending, or mixing operation if conducted in accordance with this disclosure with the application of common sense and the ordinary skill of one in the relevant art (e.g., chemist). The transformation of chemical reactants or starting materials to chemical products or final materials is a continually evolving process, independent of the speed at which it occurs. Accordingly, as such a transformative process is in progress there may be a mix of starting and final materials, as well as intermediate species that may be, depending on their kinetic lifetime, easy or difficult to detect with current analytical techniques known to those of ordinary skill in the art.

Reactants and components referred to by chemical name or formula in the specification or claims hereof, whether referred to in the singular or plural, may be identified as they exist prior to coming into contact with another substance referred to by chemical name or chemical type (e.g., another reactant or a solvent). Preliminary and/or transitional chemical changes, transformations, or reactions, if any, that take place in the resulting mixture, solution, or reaction medium may be identified as intermediate species, master batches, and the like, and may have utility distinct from the utility of the reaction product or final material. Other subsequent changes, transformations, or reactions may result from bringing the specified reactants and/or components together under the conditions called for pursuant to this disclosure. In these other subsequent changes, transformations, or reactions the reactants, ingredients, or the components to be brought together may identify or indicate the reaction product or final material.

In describing the products of the instant invention as a reaction product of initial materials reference is made to the initial species recited and it is to be noted that additional materials may be added to the initial mixture of synthetic precursors. These additional materials may be reactive or non-reactive. The defining characteristic of the instant invention is that the reaction product is obtained from the reaction of at least the components listed as disclosed. Non-reactive components may be added to the reaction mixture as diluents or to impart additional properties unrelated to the properties of the composition prepared as a reaction product. Thus for example finely divided solids such as pigments may be dispersed into the reaction mixture, before during or after reaction to produce a reaction product composition that additionally comprises the non-reactive component, e.g. a pigment. Additional reactive components may also be added; such components may react with the initial reactants or they may react with the reaction product; the phrase "reaction product" is intended to include those possibilities as well as including the addition of non-reactive components.

Optionally the reaction of component A with component B can be conducted in the presence of a primary or secondary amine that may or may not possess a reactive alkoxy silane moiety. The result will be a reaction product of A, B, and the primary or secondary amine. Examples of these primary amines are; methylamine, ethylamine, propylamine, ethanol amine, isopropylamine, butylamine, isobutylamine, hexylamine, dodecylamine, oleylamine, aniline aminopropyltrimethylsilane, aminopropyltriethylsilane, aminomorpholine, aminopropyldiethylamine benzylamine, napthylamine 3-amino-9-ethylcarbazole, 1-aminoheptaphlorohexane, 2,2,3,3,4,4,5,5,6,6,7,7,8,8-pentadecafluoro-1-octanamine and the like. Examples of secondary amines are; methylethylamine, methylhexylamine, methyloctadecylamine, diethanolamine, dibenzylamine, dihexylamine dicyclohexylamine, piperidine, pyrrolidine phthalimide, and the like. Polymeric amines may also be used such.

Applications for Embodiments of the Invention

The product of the reaction of A, an oxirane or oxetane compound possessing two or more oxirane or oxetane groups per molecule and B, an aminosilane, results in a polymer that contains alkoxy silane functional moieties covalently bond to the polymer chain. These alkoxy silane groups may be activated particularly by hydrolysis and undergo further reactions leading to a cross-linked network. The cross-linking mechanism of silanes is usually a two-step process. The first step usually involves the hydrolysis of an alkoxy silane to form silanols. The second step usually involves the condensation of the silanol groups so produced with themselves or with other reactive organic groups. The reaction between two silanol groups leads to a thermally stable siloxane bond. Silanol groups may also condense reversibly with organic moieties such as alcohols, carboxylic acids, amines, mercaptans, and ketones (other reactive groups). The bonds that are formed are less stable than the siloxane bonds. However when a cross-linked network is formed the rate of the reverse reaction may be severely reduced or even stopped.

The compositions of the present invention may be utilized as pure components, mixtures, or emulsions. As is generally known, emulsions comprise at least two immiscible phases one of which is continuous and the other which is discontinuous. Further emulsions may be liquids or gases with varying viscosities or solids. Additionally the particle size of the emulsions may render them microemulsions and when sufficiently small microemulsions may be transparent. Further it is also possible to prepare emulsions of emulsions and these are generally known as multiple emulsions. These emulsions may be:

aqueous emulsions where the discontinuous phase comprises water and the continuous phase comprises the composition of the present invention;

aqueous emulsions where the discontinuous phase comprises the composition of the present invention and the continuous phase comprises water;

non-aqueous emulsions where the discontinuous phase comprises a non-aqueous hydroxylic solvent and the continuous phase comprises the composition of the present invention; and non-aqueous emulsions where the continuous phase comprises a non-aqueous hydroxylic organic solvent and the discontinuous phase comprises the composition of the present invention.

Depending on the choice of component A and component B it is possible to alter the hydrophilic or lipophilic properties of the resulting reaction product. Thus depending on the hydrophilic lipophilic balance, the resulting reaction product may be soluble in polar aqueous or hydroxylic solvents or it may be soluble in non-polar solvents such as oils, low molecular weight siloxanes and silicones and the like.

A. Agricultural Uses

Pesticide—Agriculture, Horticulture, Turf, Ornamental and Forestry:

Many pesticide applications require the addition of an adjuvant to the spray mixture to provide wetting and spreading on foliar surfaces. Often that adjuvant is a surfactant, which can perform a variety of functions, such as increasing spray droplet retention on difficult to wet leaf surfaces, enhance spreading to improve spray coverage, or to provide penetration of the herbicide into the plant cuticle. These adjuvants are provided either as a tank-side additive or used as a component in pesticide formulations.

Typical uses for pesticides include agricultural, horticultural, turf, ornamental, home and garden, veterinary and forestry applications.

The pesticidal compositions of the present invention also include at least one pesticide, where the composition of the present invention is present at an amount sufficient to deliver between 0.005% and 2% to the final use concentration, either as a concentrate or diluted in a tank mix. Optionally the pesticidal composition may include excipients, cosurfactants, solvents, foam control agents, deposition aids, drift retardants, biologicals, micronutrients, fertilizers and the like. The term pesticide means any compound used to destroy pests, e.g., rodenticides, insecticides, miticides, fungicides, and herbicides. Illustrative examples of pesticides that can be employed include, but are not limited to, growth regulators, photosynthesis inhibitors, pigment inhibitors, mitotic disrupters, lipid biosynthesis inhibitors, cell wall inhibitors, and cell membrane disrupters. The amount of pesticide employed in compositions of the invention varies with the type of pesticide employed. More specific examples of pesticide compounds that can be used with the compositions of the invention are, but not limited to, herbicides and growth regulators, such as: phenoxy acetic acids, phenoxy propionic acids, phenoxy butyric acids, benzoic acids, triazines and s-triazines, substituted ureas, uracils, bentazon, desmedipham, methazole, phenmedipham, pyridate, amitrole, clomazone, fluridone, norflurazone, dinitroanilines, isopropalin, oryzalin, pendimethalin, prodiamine, trifluralin, glyphosate, sulfonylureas, imidazolinones, clethodim, diclofop-methyl, fenoxaprop-ethyl, fluazifop-p-butyl, haloxyfop-methyl, quizalofop, sethoxydim, dichlobenil, isoxaben, and bipyridylium compounds.

Fungicide compositions that can be used with the present invention include, but are not limited to, aldimorph, tridemorph, dodemorph, dimethomorph; flusilazol, azaconazole, cyproconazole, epoxiconazole, furconazole, propiconazole, tebuconazole and the like; imazalil, thiophanate, benomyl carbendazim, chlorothialonil, dicloran, trifloxystrobin, fluoxystrobin, dimoxystrobin, azoxystrobin, furcaranil, prochloraz, flusulfamide, famoxadone, captan, maneb, mancozeb, dodicin, dodine, and metalaxyl.

Insecticide, larvacide, miticide and ovacide compounds that can be used with the composition of the present invention, but not limited to, *Bacillus thuringiensis*, spinosad, abamectin, doramectin, lepimectin, pyrethrins, carbaryl, primicarb, aldicarb, methomyl, amitraz, boric acid, chlordimeform, novaluron, bistrifluron, triflumuron, diflubenzuron, imidacloprid, diazinon, acephate, endosulfan, kelevan, dimethoate, azinphos-ethyl, azinphos-methyl, izoxathion, chlorpyrifos, clofentezine, lambda-cyhalothrin, permethrin, bifenthrin, cypermethrin and the like.

Fertilizers and Micronutrients:

Fertilizers and micronutrients include, but are not limited to, zinc sulfate, ferrous sulfate, ammonium sulfate, urea, urea ammonium nitrogen, ammonium thiosulfate, potassium sulfate, monoammonium phosphate, urea phosphate, calcium nitrate, boric acid, potassium and sodium salts of boric acid, phosphoric acid, magnesium hydroxide, manganese carbonate, calcium polysulfide, copper sulfate, manganese sulfate, iron sulfate, calcium sulfate, sodium molybdate, calcium chloride, The pesticide or fertilizer may be a liquid or a solid. If a solid, it is preferable that it is soluble in a solvent, or the organomodified disiloxanes of the present invention, prior to application, and the silicone may act as a solvent, or surfactant for such solubility or additional surfactants may perform this function.

Agricultural Excipients:

Buffers, preservatives and other standard excipients known in the art also may be included in the composition.

Solvents may also be included in compositions of the present invention. These solvents are in a liquid state at room temperature. Examples include water, alcohols, aromatic solvents, oils (i.e. mineral oil, vegetable oil, silicone oil, and so forth), lower alkyl esters of vegetable oils, fatty acids, ketones, glycols, polyethylene glycols, diols, paraffinics, and so forth. Particular solvents would be 2, 2, 4-trimethyl, 1-3-pentane diol and alkoxylated (especially ethoxylated) versions thereof as illustrated in U.S. Pat. No. 5,674,832 herein incorporated by reference, or n-methyl-pyrrilidone.

Cosurfactants:

Cosurfactants useful herein include nonionic, cationic, anionic, amphoteric, zwitterionic, polymeric surfactants, or any mixture thereof. Surfactants are typically hydrocarbon based, silicone based or fluorocarbon based.

Moreover, other cosurfactants, that have short chain hydrophobes that do not interfere with superspreading as described in U.S. Pat. No. 5,558,806 herein incorporated by reference are also useful. Additionally, the compositions described above are also useful as the alkyl chloride, alkyl iodide and alkyl bromide analogues, as well as the acid pairs with HCl, acetic acid, propionic acid, glycolic acid, gibberellic acid and the like. One skilled in the art understands the benefits of quaternizernization, which increases solubility and as well as makes possible potential interactions with nonionic and anionic cosurfactants.

Useful surfactants include alkoxylates, especially ethoxylates, containing block copolymers including copolymers of ethylene oxide, propylene oxide, butylene oxide, and mixtures thereof; alkylarylalkoxylates, especially ethoxylates or propoxylates and their derivatives including alkyl phenol ethoxylate; arylarylalkoxylates, especially ethoxylates or propoxylates. and their derivatives; amine alkoxylates, especially amine ethoxylates; fatty acid alkoxylates; fatty alcohol alkoxylates; alkyl sulfonates; alkyl benzene and alkyl naphthalene sulfonates; sulfated fatty alcohols, amines or acid amides; acid esters of sodium isethionate; esters of sodium sulfosuccinate; sulfated or sulfonated fatty acid esters; petroleum sulfonates; N-acyl sarcosinates; alkyl polyglycosides; alkyl ethoxylated amines; and so forth.

Specific examples include alkyl acetylenic diols (SURFONYL—Air Products), pyrrilodone based surfactants (e.g., SURFADONE—LP 100—ISP), 2-ethyl hexyl sulfate, isodecyl alcohol ethoxylates (e.g., RHODASURF DA 530—Rhodia), ethylene diamine alkoxylates (TETRONICS—BASF), ethylene oxide/propylene oxide copolymers (PLURONICS—BASF), Gemini type surfactants (Rhodia) and diphenyl ether Gemini type surfactants (e.g. DOWFAX—Dow Chemical).

Preferred surfactants include ethylene oxide/propylene oxide copolymers (EO/PO); amine ethoxylates; alkyl polyglycosides; oxo-tridecyl alcohol ethoxylates, and so forth.

In a preferred embodiment, the agrochemical composition of the present invention further comprises one or more agrochemical ingredients. Suitable agrochemical ingredients include, but not limited to, herbicides, insecticides, growth regulators, fungicides, miticides, acaricides, fertilizers, biologicals, plant nutritionals, micronutrients, biocides, paraffinic mineral oil, methylated seed oils (i.e. methylsoyate or methylcanolate), vegetable oils (such as soybean oil and canola oil), water conditioning agents such as Choice® (Loveland Industries, Greeley, Colo.) and Quest (Helena Chemical, Collierville, Tenn.), modified clays such as Surround® (Englehard Corp.,), foam control agents, surfactants, wetting agents, dispersants, emulsifiers, deposition aids, anti-drift components, and water.

Suitable agrochemical compositions are made by combining, in a manner known in the art, such as, by mixing one or more of the above components with the organomodified disiloxane of the present invention, either as a tank-mix, or as an "In-can" formulation. The term "tank-mix" means the addition of at least one agrochemical to a spray medium, such as water or oil, at the point of use. The term "In-can" refers to a formulation or concentrate containing at least one agrochemical component. The "In-can" formulation may then diluted to use concentration at the point of use, typically in a Tank-mix, or it may be used undiluted.

B. Coatings

Typically coatings formulations will require a wetting agent or surfactant for the purpose of emulsification, compatibilization of components, leveling, flow and reduction of surface defects. Additionally, these additives may provide improvements in the cured or dry film, such as improved abrasion resistance, antiblocking, hydrophilic, and hydrophobic properties. Coatings formulations may exists as, Solvent-borne coatings, water-borne coatings and powder coatings.

The coatings components may be employed as: architecture coatings; OEM product coatings such as automotive coatings and coil coatings; Special Purpose coatings such as industrial maintenance coatings and marine coatings;

Typical resin types include: Polyesters, alkyds, acrylics, epoxies

C. Personal Care

In a preferred embodiment, the epoxy amino silane copolymers of the present invention comprises, per 100 parts by weight ("pbw") of the personal care composition, from 0.1 to 99 pbw and more preferably from 0.5 pbw to 30 pbw and still more preferably from 1 to 15 pbw of the composition of the present invention and from 1 pbw to 99.9 pbw, more preferably from 70 pbw to 99.5 pbw, and still more preferably from 85 pbw to 99 pbw of the personal care composition.

The compositions of the present invention may be utilized in personal care emulsions, such as lotions, and creams. As is generally known, emulsions comprise at least two immiscible phases one of which is continuous and the other which is discontinuous. Further emulsions may be liquids with varying viscosities or solids. Additionally the particle size of the emulsions may render them microemulsions and, when sufficiently small, microemulsions may be transparent. Further it is also possible to prepare emulsions of emulsions and these are generally known as multiple emulsions. These emulsions may be:

1) aqueous emulsions where the discontinuous phase comprises water and the continuous phase comprises the epoxy amino silane copolymers of the present invention;

2) aqueous emulsions where the discontinuous phase comprises the epoxy amino silane copolymers of the present invention and the continuous phase comprises water;

3) non-aqueous emulsions where the discontinuous phase comprises a non-aqueous hydroxylic solvent and the continuous phase comprises the epoxy amino silane copolymers of the present invention; and 4) non-aqueous emulsions where the continuous phase comprises a non-aqueous hydroxylic organic solvent and the discontinuous phase comprises the epoxy amino silane copolymers of the present invention.

Non-aqueous emulsions comprising a silicone phase are described in U.S. Pat. Nos. 6,060,546 and 6,271,295 the disclosures of which are herewith and hereby specifically incorporated by reference.

As used herein the term "non-aqueous hydroxylic organic compound" means hydroxyl containing organic compounds exemplified by alcohols, glycols, polyhydric alcohols and polymeric glycols and mixtures thereof that are liquid at room temperature, e.g. about 25° C., and about one atmosphere pressure. The non-aqueous organic hydroxylic solvents are selected from the group consisting of hydroxyl containing organic compounds comprising alcohols, glycols, polyhydric alcohols and polymeric glycols and mixtures thereof that are liquid at room temperature, e.g. about 25° C., and about one atmosphere pressure. Preferably the non-aqueous hydroxylic organic solvent is selected from the group consisting of ethylene glycol, ethanol, propyl alcohol, iso-propyl alcohol, propylene glycol, dipropylene glycol, tripropylene glycol, butylene glycol, iso-butylene glycol, methyl propane diol, glycerin, sorbitol, polyethylene glycol, polypropylene glycol mono alkyl ethers, polyoxyalkylene copolymers and mixtures thereof.

Once the desired form is attained whether as a silicone only phase, an anhydrous mixture comprising the silicone phase, a hydrous mixture comprising the silicone phase, a water-in-oil emulsion, an oil-in-water emulsion, or either of the two non-aqueous emulsions or variations thereon, the resulting material is usually a cream or lotion with improved deposition properties and good feel characteristics. It is capable of being blended into formulations for hair care, skin care, antiperspirants, sunscreens, cosmetics, color cosmetics, insect repellents, vitamin and hormone carriers, fragrance carriers and the like.

The personal care applications where the epoxy amino silane copolymers of the present invention and the silicone compositions derived therefrom of the present invention may be employed include, but are not limited to, deodorants, antiperspirants, antiperspirant/deodorants, shaving products, skin lotions, moisturizers, toners, bath products, cleansing products, hair care products such as shampoos, conditioners, mousses, styling gels, hair sprays, hair dyes, hair color products, hair bleaches, waving products, hair straighteners, manicure products such as nail polish, nail polish remover, nails creams and lotions, cuticle softeners, protective creams such as sunscreen, insect repellent and anti-aging products, color cosmetics such as lipsticks, foundations, face powders, eye liners, eye shadows, blushes, makeup, mascaras and other personal care formulations where silicone components have been conventionally added, as well as drug delivery systems for topical application of medicinal compositions that are to be applied to the skin.

In a preferred embodiment, the personal care composition of the present invention further comprises one or more personal care ingredients. Suitable personal care ingredients include, for example, emollients, moisturizers, humectants, pigments, including pearlescent pigments such as, for example, bismuth oxychloride and titanium dioxide coated mica, colorants, fragrances, biocides, preservatives, antioxidants, anti-microbial agents, anti-fungal agents, antiperspirant agents, exfoliants, hormones, enzymes, medicinal compounds, vitamins, salts, electrolytes, alcohols, polyols, absorbing agents for ultraviolet radiation, botanical extracts, surfactants, silicone oils, organic oils, waxes, film formers, thickening agents such as, for example, fumed silica or hydrated silica, particulate fillers, such as for example, talc, kaolin, starch, modified starch, mica, nylon, clays, such as, for example, bentonite and organo-modified clays.

Suitable personal care compositions are made by combining, in a manner known in the art, such as, for example, by mixing, one or more of the above components with the compositions of the present invention. Suitable personal care compositions may be in the form of a single phase or in the form of an emulsion, including oil-in-water, water-in-oil and anhydrous emulsions where the silicone phase may be either the discontinuous phase or the continuous phase, as well as multiple emulsions, such as, for example, oil-in water-in-oil emulsions and water-in-oil-in water-emulsions.

In one useful embodiment, an antiperspirant composition comprises the epoxy amino silane copolymers of the present invention and one or more active antiperspirant agents. Suitable antiperspirant agents include, for example, the Category I active antiperspirant ingredients listed in the U.S. Food and Drug Administration's Oct. 10, 1993 Monograph on antiperspirant drug products for over-the-counter human use, such as, for example, aluminum halides, aluminum hydroxyhalides, for example, aluminum chlorohydrate, and complexes or mixtures thereof with zirconyl oxyhalides and zirconyl hydroxyhalides, such as for example, aluminum-zirconium chlorohydrate, aluminum zirconium glycine complexes, such as, for example, aluminum zirconium tetrachlorohydrex gly.

In another useful embodiment, a skin care composition comprises the compositions of the present invention, and a vehicle, such as, for example, a silicone oil or an organic oil. The skin care composition may, optionally, further include emollients, such as, for example, triglyceride esters, wax esters, alkyl or alkenyl esters of fatty acids or polyhydric alcohol esters and one or more the known components conventionally used in skin care compositions, such as, for example, pigments, vitamins, such as, for example, Vitamin A, Vitamin C and Vitamin E, sunscreen or sunblock compounds, such as, for example, titanium dioxide, zinc oxide, oxybenzone, octylmethoxy cinnamate, butylmethoxy dibenzoylm ethane, p-aminobenzoic acid and octyl dimethyl-p-aminobenzoic acid.

In another useful embodiment, a color cosmetic composition, such as, for example, a lipstick, a makeup or a mascara composition comprises the compositions of the present invention, and a coloring agent, such as a pigment, a water soluble dye or a liposoluble dye.

In another useful embodiment, the compositions of the present invention are utilized in conjunction with fragrant materials. These fragrant materials may be fragrant compounds, encapsulated fragrant compounds, or fragrance releasing compounds that either the neat compounds or are encapsulated. Particularly compatible with the compositions of the present invention are the fragrance releasing silicon containing compounds as disclosed in U.S. Pat. Nos. 6,046,156; 6,054,547; 6,075,111; 6,077,923; 6,083,901; and 6,153,578; all of which are herein and herewith specifically incorporated by reference.

The uses of the compositions of the present invention are not restricted to personal care compositions, other products such as waxes, polishes and textiles treated with the compositions of the present invention are also contemplated.

D. Home Care

Home care applications include laundry detergent and fabric softener, dishwashing liquids, wood and furniture polish, floor polish, tub and tile cleaners, toilet bowl cleaners, hard surface cleaners, window cleaners, antifog agents, drain cleaners, auto-dish washing detergents and sheeting agents, carpet cleaners, prewash spotters, rust cleaners and scale removers.

E. Oil and Gas

Compositions of the present organomodified silylated surfactant invention are useful in oil and gas applications, including demulsification.

F. Water Processing

Compositions comprising organomodified silylated surfactant invention are useful for applications involving commercial and industrial open recirculating cooling water towers, closed cooling water systems, cooling water conduits, heat exchangers, condensers, once-through cooling systems, Pasteurizers, air washers, heat exchange systems, air conditioning/humidifiers/dehumidifiers, hydrostatic cookers, safety and/or fire water protection storage systems, water scrubbers, disposal wells, influent water systems, including filtration and clarifiers, wastewater treatment, wastewater treatment tanks, conduits, filtration beds, digesters, clarifiers, holding ponds, settling lagoons, canals, odor control, ion exchange resin beds, membrane filtration, reverse osmosis, micro- and ultra-filtration, assisting in the removal of biofilms in cooling tower applications, heat exchangers and process water systems, and the like.

G. Pulp and Paper

Compositions of the present organomodified silylated surfactant invention are useful in pulp and paper applications, such as paperboard defoamers, and wetting agents for the pulping process.

EXPERIMENTAL

SYNTHETIC EXAMPLES

Example A

An epoxy encapped polyether (148.28 g) with the average structure of $CH_2(O)CHCH_2O(CH_2CH_2O)_{22}CH_2CH(O)CH_2$, aminopropyltriisopropoxysilane (51.72 g) and isopropanol (60.00 g) were combined in a 500 mL round bottom flask. The solution was heat to reflux and stirred with a magnetic stirrer. The reaction was allowed to remain at reflux until all the epoxy groups were consumed as determined by titration. The resulting material exhibited a dark straw color. The material was transferred to a rotary evaporator and stripped at 70° C. and 4 torr for 2 hrs to remove the isopropanol.

Example B

Aminopropyltriisopropoxy silane (51.72 g), an epoxy encapped polyether with the average structure $CH_2(O)CHCH_2(OCH_2CH_2)_{7.3}OCH_2CH(O)CH_2$ (148.28 g) and isopropanol (60.00 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example C

Aminopropyltriisopropoxy silane (40.3 g), an epoxy encapped polysiloxane with the average structure $CH_2(O)CHCH_2OCH_2CH_2CH_2Si(CH_3)_2O[Si(CH_3)_2O]_{50}Si(CH_3)_2CH_2CH_2CH_2OCH(O)CH_2$ (206.12 g) and an epoxy encapped polyether with the average structure $CH_2(O)CHCH_2O(CH_2(CH_3)CH_2O)_7CH_2CH(O)CH_2$ (18.67 g) and isopropanol (88.48 g) was combined in a 500 mL flask. The material was brought to reflux and stirred with an overhead stirrer. The refluxing continued for 15.5 hr until all epoxy groups were consumed as determined by titration. The material was transferred to a rotary evaporator and stripped at 70° C. and 4 torr for 2 hrs to remove the isopropanol.

Example D

Aminopropyltriisopropoxy silane (54.27 g), an epoxy encapped polysiloxane with the average structure $CH_2(O)CHCH_2OCH_2CH_2CH_2Si(CH_3)_2O[Si(CH_3)_2O]_{50}-Si(CH_3)_2CH_2CH_2CH_2OCH(O)CH_2$ (185.70 g) and an epoxy encapped polyether with the average structure $CH_2(O)CHCH_2O(CH_2CH_2O)_7CH_2CH(O)CH_2$ (49.74 g) and isopropanol (507.39 g) was combined in a 1 L flask. The material was brought to reflux and stirred with an overhead stirrer. The refluxing continued for 16 hr until all epoxy groups were consumed as determined by titration. The material was transferred to a rotary evaporator and stripped at 70° C. and 4 torr for 2 hrs to remove the isopropanol.

Example E

Aminopropyltriisopropoxy silane (53.94 g), Bisphenol A Diglycidyl Ether (46.09 g), and isopropanol (25.01 g) was combined in a 250 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example F

Aminopropyltriisopropoxy silane (59.22 g), 1,7-diepoxy octane (20.40 g), an epoxy encapped polysiloxane with the average structure $CH_2(O)CHCH_2OCH_2CH_2CH_2Si(CH_3)_2O[Si(CH_3)_2O]_{50}-Si(CH_3)_2CH_2CH_2CH_2OCH(O)CH_2$ (20.41 g) and isopropanol (25.01 g) was combined in a 250 mL flask. The material was brought to reflux and stirred with an overhead stirrer. The refluxing continued for 16 hr until all epoxy groups were consumed as determined by titration. The material was transferred to a rotary evaporator and stripped at 70° C. and 4 torr for 2 hrs to remove the isopropanol.

Example G

Aminopropyltriisopropoxy silane (41.48 g), 1,6-hexanediol diglycidyl ether (29.43 g), an epoxy encapped polysiloxane with the average structure $CH_2(O)CHCH_2OCH_2CH_2CH_2Si(CH_3)_2O[Si(CH_3)_2O]_{50}-Si(CH_3)_2CH_2CH_2CH_2OCH(O)CH_2$ (29.26 g) and isopropanol (110.01 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example H

Aminopropyltriisopropoxy silane (34.07 g), hydrogenated bisphenol A diglycidyl ether (32.98 g), an epoxy encapped polysiloxane with the average structure $CH_2(O)CHCH_2OCH_2CH_2CH_2Si(CH_3)_2O[Si(CH_3)_2O]_{50}-Si(CH_3)_2CH_2CH_2CH_2OCH(O)CH_2$ (32.96 g) and isopropanol (110.08 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example I

Aminopropyltriisopropoxy silane (12.94 g), an epoxy encapped polysiloxane with the average structure $CH_2(O)CHCH_2OCH_2CH_2CH_2Si(CH_3)_2O[Si(CH_3)_2O]_{25}-Si(CH_3)_2CH_2CH_2CH_2OCH(O)CH_2$ (87.06 g) and isopropanol (30.0 g) was combined in a 250 mL flask. The material was brought to reflux and stirred with an overhead stirrer. The refluxing continued for 16 hr until all epoxy groups were consumed as determined by titration. The material was transferred to a rotary evaporator and stripped at 70° C. and 4 torr for 2 hrs to remove the isopropanol. The material obtained was a clear straw colored liquid.

Example J

Aminopropyltriisopropoxy silane (27.00 g), an epoxy encapped polysiloxane with the average structure $CH_2(O)CHCH_2OCH_2CH_2CH_2Si(CH_3)_2O[Si(CH_3)_2O]_{50}-Si(CH_3)_2CH_2CH_2CH_2OCH(O)CH_2$ (92.70 g), an epoxy encapped polyether with the average structure $CH_2(O)CHCH_2O(CH_2CH_2O)_7CH_2CH(O)CH_2$ (27.69 g) and isopropanol (253.43 g) was combined in a 500 mL flask. The material was brought to reflux and stirred with an overhead stirrer. The refluxing continued for 16 hr until all epoxy groups were consumed as determined by titration. The material was transferred to a rotary evaporator and stripped at 70° C. and 4 torr for 2 hrs to remove the isopropanol.

Example K

Aminopropyltriisopropoxy silane (11.20 g), polybutadiene diglycidyl ether (Mw 3150 g/mol) and isopropanol (100.0 g) was combined in a 500 mL flask. The material was brought to reflux and stirred with an overhead stirrer. The refluxing continued for 23 hr until all epoxy groups were consumed as determined by titration. The material was transferred to a rotary evaporator and stripped at 70° C. and 4 torr for 2 hrs to remove the isopropanol. The material obtained was a viscous clear straw colored liquid.

Example L

Aminopropyltriisopropoxy silane (75.22 g), an epoxy encapped polyether with the average structure $CH_2(O)CHCH_2(OCH_2CH_2)_{6.9}OCH_2CH(O)CH_2$ (124.81 g) and isopropanol (60.00 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example M

Aminopropyltriisopropoxy silane (71.31 g), an epoxy encapped polyether with the average structure $CH_2(O)CHCH_2(OCH_2CH_2)_{11.7}OCH_2CH(O)CH_2$ (128.69 g) and isopropanol (60.00 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example N

Aminopropyltriisopropoxy silane (40.34 g), an epoxy encapped polysiloxane with the average structure $CH_2(O)CHCH_2OCH_2CH_2CH_2Si(CH_3)_2O[Si(CH_3)_2O]_5$—$Si(CH_3)_2CH_2CH_2CH_2OCH(O)CH_2$ (9.66 g), an epoxy encapped polyether with the average structure $CH_2(O)CHCH_2O(CH_2CH_2O)_{7.7}CH_2CH(O)CH_2$ (50.00 g) and isopropanol (21.01 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example O

Aminopropyltriisopropoxy silane (42.90 g), an epoxy encapped polysiloxane with the structure $CH_2(O)CHCH_2OCH_2CH_2CH_2Si(CH_3)_2OSi(CH_3)_2CH_2CH_2CH_2OCH(O)CH_2$ (7.11 g), an epoxy encapped polyether with the average structure $CH_2(O)CHCH_2O(CH_2CH_2O)_{7.7}CH_2CH(O)CH_2$ (50.02 g) and isopropanol (20.01 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example P

Aminopropyltriisopropoxy silane (27.00 g), an epoxy encapped polysiloxane with the structure $CH_2(O)CHCH_2OCH_2CH_2CH_2Si(CH_3)_2O[Si(CH_3)_2O]_{50}$—$Si(CH_3)_2CH_2CH_2CH_2OCH(O)CH_2$ (52.14 g), an epoxy encapped polyether with the average structure $CH_2(O)CHCH_2O(CH_2CH_2O)_9CH_2CH(O)CH_2$ (48.60 g) and isopropanol (200.00 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example Q

Aminopropyltriisopropoxy silane (27.00 g), an epoxy encapped polysiloxane with the structure $CH_2(O)CHCH_2OCH_2CH_2CH_2Si(CH_3)_2O[Si(CH_3)_2O]_{50}Si(CH_3)_2CH_2CH_2CH_2OCH(O)CH_2$ (13.90 g), an epoxy encapped polyether with the average structure $CH_2(O)CHCH_2O(CH_2CH_2O)_{7.7}CH_2CH(O)CH_2$ (53.69 g) and isopropanol (20.01 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example R

Aminopropyltriisopropoxy silane (71.31 g), an epoxy encapped polyether with the average structure $CH_2(O)CHCH_2(OCH_2CH_2)_{11.7}OCH_2CH(O)CH_2$ (128.69 g) and isopropanol (60.00 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example S

Aminopropyltriisopropoxy silane (15.02 g), an epoxy encapped polysiloxane with the structure $CH_2(O)CHCH_2OCH_2CH_2CH_2Si(CH_3)_2O[Si(CH_3)_2O]_{100}Si(CH_3)_2CH_2CH_2CH_2OCH(O)CH_2$ (98.42 g), an epoxy encapped polyether with the average structure $CH_2(O)CHCH_2O(CH_2CH_2O)_{21.7}CH_2CH(O)CH_2$ (36.56 g) and isopropanol (1500.01 g) was combined in a 500 mL flask. The material was brought to reflux and stirred with an overhead stirrer. The refluxing continued for 24 hr until all epoxy groups were consumed as determined by titration. The material was transferred to a rotary evaporator and stripped at 70° C. and 4 torr for 2 hrs to remove the isopropanol.

Example T

An epoxy end capped polyether (59.37 g) with the average structure of $CH_2(O)CHCH_2O(CH_2CH_2O)_{11.2}CH_2CH(O)CH_2$, aminopropyltriisopropoxysilane (24.38 g), aminopropyltriethylsilane (16.25 g) and isopropanol (100 g) were combined in a 500 mL round bottom flask. The solution was heat to reflux and stirred with a magnetic stirrer. The reaction was allowed to remain at reflux until all the epoxy groups were consumed as determined by titration. The resulting material exhibited a dark straw color. The material was transferred to a rotary evaporator and stripped at 70° C. and 4 torr for 2 hrs to remove the isopropanol.

Example U

An epoxy end capped polyether (34.56 g) with the average structure of $CH_2(O)CHCH_2O(CH_2CH_2O)_{11.2}CH_2CH(O)$ $CH_2$, aminopropyltriisopropoxysilane (14.75 g), oleylamine (0.70 g) and isopropanol (50 g) were combined in a 250 mL round bottom flask. The solution was heat to reflux and stirred with a magnetic stirrer. The reaction was allowed to remain at reflux until all the epoxy groups were consumed as determined by titration. The resulting material exhibited a dark straw color. The material was transferred to a rotary evaporator and stripped at 70° C. and 4 torr for 2 hrs to remove the isopropanol.

Example V

An epoxy end capped polyether (34.92 g) with the average structure of $CH_2(O)CHCH_2O(CH_2CH_2O)_{11.2}CH_2CH(O)CH_2$, aminopropyltriisopropoxysilane (14.58 g), ethylhexylamine (0.49 g) and isopropanol (50 g) were combined in a 250 mL round bottom flask. The solution was heat to reflux and stirred with a magnetic stirrer. The reaction was allowed to remain at reflux until all the epoxy groups were consumed as determined by titration. The resulting material exhibited a dark straw color. The material was transferred to a rotary evaporator and stripped at 70° C. and 4 torr for 2 hrs to remove the isopropanol.

Coatings Application Examples

Coating of the substrate for Examples 1-4

The products from synthesis examples A, B, C and D were made using the following method. Example A, B, C or D (5 g) was added to 20 g of distilled water. The solution was mixed with a magnetic stir bar and neutralized to pH 7 with acetic acid. The resulting formulation a listed in the table below. Example formulations numbered 1-4 were coated on cleaned and dried untreated steal plates. The coating was conducted using a 3 mil wire wound rod. 5 mL of each formulation was added to the substrate in front of the rod. The rod was pulled across the substrate at constant force and velocity. The coating was allowed to cure for 4 days at room temperature.

|  | Example Formulation 1 | Example Formulation 2 | Example Formulation 3 | Example Formulation 4 |
|---|---|---|---|---|
| Example A | 20% | — | — | — |
| Example B | — | 20% | — | — |
| Example C | — | — | 20% | — |
| Example D | — | — | — | 20% |
| Water | 80% | 80% | 80% | 80% |
| Appearance | Milky | Clear | Milky | Bluish White |

Application Example 1 Gloss

Using the procedure from the ASTM standard test method (D 4039-87) was used. Both 20° and 60° specular gloss was taken and is shown in the table below. Two panels were coated and the gloss was measured.

|  |  |  | Gloss | |
|---|---|---|---|---|
| Substrate | Cure Conditions | 20° | 60° |
| Example Formulation 1 | Untreated Steel | Room Temp 4 days | 19 | 45.4 |
| Example Formulation 1 | Untreated Steel | Room Temp 4 days | 14.1 | 35.1 |
| Example Formulation 2 | Untreated Steel | Room Temp 4 days | 10.8 | 21.7 |
| Example Formulation 2 | Untreated Steel | Room Temp 4 days | 11.4 | 22.2 |
| Example Formulation 3 | Untreated Steel | Room Temp 4 days | 23.4 | 47.1 |
| Example Formulation 3 | Untreated Steel | Room Temp 4 days | 24.6 | 50.1 |
| Example Formulation 4 | Untreated Steel | Room Temp 4 days | 14.7 | 38.3 |
| Example Formulation 4 | Untreated Steel | Room Temp 4 days | 15.3 | 38.2 |

Application Example 2 Pencil Hardness

Using the procedure from the standard test method for film hardness by pencil test (ASTM D3363-74) was followed. The treated steal panel was subject to multiple scratches using various hardness pencils. The results are given in the table below. The rating was based on scratch hardness or the hardest pencil that will not rupture or scratch the film.

|  | Substrate | Cure Conditions | Pencil Harness |
|---|---|---|---|
| Example Formulation 1 | Untreated Steel | Room Temp 4 days | 3H |
| Example Formulation 1 | Untreated Steel | Room Temp 4 days | 3H |
| Example Formulation 2 | Untreated Steel | Room Temp 4 days | 2B |
| Example Formulation 2 | Untreated Steel | Room Temp 4 days | 2B |
| Example Formulation 3 | Untreated Steel | Room Temp 4 days | 3H |
| Example Formulation 3 | Untreated Steel | Room Temp 4 days | 3H |
| Example Formulation 4 | Untreated Steel | Room Temp 4 days | 3H |
| Example Formulation 4 | Untreated Steel | Room Temp 4 days | 3H |

Application Example 3 Cross Hatch Adhesion

Using the procedure from the standard test method measuring adhesion by tape test (ASTM D3359-87) the cross-hatch adhesion performance was evaluated. The example formulations were coated on untreated steel and allowed to cure at room temperature for 4 days. Test method B was employed where a lattice pattern was scratched into the film. The tape was applied to the scratched surface then removed. The resulting coating was evaluated for pealing and missing portion of film. No such defects were detected when all four example formulations were tested.

Application Example 4 Solvent Resistance

Using the standard test method for measuring methyl ethyl ketone (MEK) resistance (ASTM D4752-87) was employed. The coated steel substrates were first washed with deionized water and the immediately insulted with an automated device equipped with a hammer-head and a saturated with MEK cheesecloth. The samples were rubbed for 15 times then examined for marring. The process was repeated using 120 oscillations and again examined for marring. The results are shown in the table below.

| | Substrate | Cure Conditions | MEK Resistance |
|---|---|---|---|
| Example Formulation 1 | Untreated Steel | Room Temp 4 days | 15 DR Some Mar |
| Example Formulation 1 | Untreated Steel | Room Temp 4 days | 120 DR Some Mar |
| Example Formulation 2 | Untreated Steel | Room Temp 4 days | 15 DR Trace Mar |
| Example Formulation 2 | Untreated Steel | Room Temp 4 days | 120 DR Some Mar |
| Example Formulation 3 | Untreated Steel | Room Temp 4 days | 15 DR Trace Mar |
| Example Formulation 3 | Untreated Steel | Room Temp 4 days | 120 DR Some Mar |
| Example Formulation 4 | Untreated Steel | Room Temp 4 days | 15 DR Some Mar |
| Example Formulation 4 | Untreated Steel | Room Temp 4 days | 120 DR Some Mar |

Application Example 5 Impact Resistance

Using a standard test method for measuring the resistance of organic coatings to the effects of rapid deformation (impact, ASTM D2794-69). The total scale for this test is 1 thru 5. 5 indicates no damage; 1 is visibly cracked. A 4 rating indicates pinpoint discoloration at the center of the impact or a crack at the rim of the circle only. The coated steel panels where impacted on the coated side (direct) and on the uncoated side (reverse). The results are given below.

| | Direct Impact 80 lbs | Direct Impact 10 lbs | Reverse Impact 80 lbs | Reverse Impact 10 lbs |
|---|---|---|---|---|
| Example Formulation 1 | 4 | 4 | 4 | 5 |
| Example Formulation 2 | 4 | 4 | 4 | 5 |
| Example Formulation 3 | 4 | 4 | 4 | 4 |
| Example Formulation 4 | 4 | 4 | 4 | 5 |

Anti-Staining Applications for Hardsurfaces Examples

The following examples demonstrate he utility of the silane ABn's for use as anti-staining coatings for the protection of hard surfaces.

Procedure for Making Coating Formulations

Synthetic Example C, J, L, & M were diluted to a 20% aqueous formulation and neutralized with acetic acid (pH 7). The hard surfaces tested in this application were Terracotta and Marble (3"×3"). Half of each tile was treated by adding 0.5 mL of the formulation to each tile. The coating was then smoothed using an applicator in order to have a uniform coating on half of each tile. The tiles were allowed to cure overnight at ambient temperature. The control formula was a commercial hard surface sealer from HG international. The following day each tile was subjected to two drops of staining solution. The stains are listed in the table below. The stains were allowed to sit at ambient temperature on the surface for 16 hr. Then the tiles were washed with a wet sponge and Dawn dishwashing detergent. Once dry the tiles were visually rated and given a score between 0-10, 0 being no residue left behind while 10 was given if a dark stain was evident. There is a marketable improvement in stain prevention when compared to the untreated tiles.

TABLE

Stain results on various substrates

Terracotta

| | Untreated | Example Formulation 5 | Example Formulation 6 | Example Formulation 7 | Example Formulation 8 | Control Formula |
|---|---|---|---|---|---|---|
| Canola Oil | 5.8 | 1.5 | 1.5 | 5.5 | 5.5 | 0.5 |
| Colored Water | 0 | 0 | 1 | 0 | 0 | 0.5 |
| Coffee | 0.1 | 0 | 0 | 0.5 | 2 | 0 |
| Ketchup | 2.2 | 1.5 | 2 | 5 | 2 | 0.5 |
| Mustard | 10 | 1.5 | 2 | 3 | 10 | 4 |
| Red Wine | 0.6 | 0.25 | 1 | 5 | 1 | 1 |
| Mineral Oil | 5.4 | 1 | 1 | 4 | 5 | 0 |
| Cherry Cool-Aid | 0.3 | 0.5 | 1 | 0.5 | 0.5 | 0.5 |

| | Untreated | Example Formulation 9N | Example Formulation 10O | Control Formula |
|---|---|---|---|---|
| Canola Oil | 7.5 | 2 | 5 | 0.5 |
| Colored Water | 0.8 | 0 | 0 | 5 |
| Coffee | 1.5 | 6 | 8 | 0.5 |
| Ketchup | 5.5 | 2 | 1 | 1 |
| Mustard | 9.3 | 2 | 3 | 9.5 |
| Red Wine | 1.3 | 3 | 6 | 1 |
| Mineral Oil | 6.5 | 1.5 | 1.5 | 0.5 |
| Cherry Cool-Aid | 0.5 | 1 | 0 | 0 |

| | Untreated | Example Formulation 9 | Example Formulation 10 | Control Formula |
|---|---|---|---|---|
| Granite | | | | |
| Canola Oil | 0 | 0 | 0 | 0 |
| Colored Water | 0 | 0 | 0 | 0 |

TABLE-continued

Stain results on various substrates

| | | | | |
|---|---|---|---|---|
| Coffee | 0 | 2 | 5 | 0 |
| Ketchup | 0 | 0 | 0 | 2 |
| Mustard | 8.8 | 0 | 0 | 0 |
| Red Wine | 5.5 | 7 | 8 | 0 |
| Mineral Oil | 0 | 0 | 0 | 0 |
| Cherry Cool-Aid | 0 | 2 | 4 | 0 |
| Marble | | | | |
| Canola Oil | 0 | 0 | 0 | 0 |
| Colored Water | 2 | 0 | 0 | 0 |
| Coffee | 5 | 1 | 0 | 0 |
| Ketchup | 0 | 0 | 0 | 0 |
| Mustard | 0.5 | 0 | 0 | 0 |
| Red Wine | 7 | 2 | 0 | 0 |
| Mineral Oil | 0 | 0 | 0 | 0 |
| Cherry Cool-Aid | 0 | 2 | 0.5 | 0.5 |

Non-Woven Application Examples

Treatment of Spun Polypropylene

The formulations were made accordingly to the table below. All formulations were neutralized with acetic acid to pH 7. Each example formula was applied to a 100% polypropylene (PP) nonwoven coverstock 100% (Spunbonded Polypropylene 22 g/m2) at 0.5% add-on at 100% pick-up. The nonwoven finish was applied to PP diaper coverstock by the padding method and drying conditions in a Werner Mathis AG dryer for 90 sec @ 105° C. After treatment the PP diaper coverstock was placed at ambient temperature for 24 hrs before any physical evaluations take place. These treated PP diaper coverstock materials were used for all the non-woven application examples.

| | Example Formulation 11 | Example Formulation 12 | Example Formulation 13 | Example Formulation 14 |
|---|---|---|---|---|
| Example C | 0.5% | — | — | — |
| Example D | — | 0.5% | — | — |
| Example L | — | — | 0.5% | — |
| Example M | — | — | — | 0.5% |
| Water | 99.5% | 99.5% | 99.5% | 99.5% |

Run-Off Application

Run-Off experiments were performed following the standard Edana 152.0-99. Given in the table is the percent run-off of a 0.9% sodium chloride solution when applied to a piece of treated spun polypropylene held at a 25° angle. Two different sets of treatments were chosen. Example formulations 11 and 12 are hydrophobic treatment while examples 13 and 14 are hydrophilic. An untreated sheet of polypropylene was used for comparison.

TABLE

Percent run off of 4 treated spun polypropylene sheets

| | Run 1 | Run 2 | Run 3 | Run 4 | Run 5 | Run 6 |
|---|---|---|---|---|---|---|
| Example Formulation 11 | 80.40% | 94.40% | 96.40% | 84.80% | 80.80% | 84.04% |
| Example Formulation 12 | 91.68% | 88.76% | 88.72% | 85.20% | 87.24% | 90.16% |
| Example Formulation 13 | 82.92% | 39.72% | 15.60% | 0.00% | 0.00% | 4.36% |
| Example Formulation 14 | 69.84% | 21.84% | 58.80% | 21.50% | 51.12% | 8.92% |
| Untreated | 93.80% | 96.04% | 95.24% | 92.00% | 97.84% | 97.24% |

Strike Through

Run-Off experiments were performed following the standard Edana Strike Through Time 150.3-96. Given in the table is the percent run-off of a 0.9% sodium chloride solution when applied to a piece of treated spun polypropylene held at a 25° angle. Two different sets of treatments were chosen. Example formulations 11 and 12 are hydrophobic treatment while examples 13 and 14 are hydrophilic. An untreated sheet of polypropylene was used for comparison.

| | Time |
|---|---|
| Example Formulation 11 | 30.56 sec |
| Example Formulation 12 | 115.01 sec |
| Example Formulation 13 | 8.87 sec |
| Example Formulation 14 | 13.05 sec |
| Untreated | 245.95 sec |

Hydrostatic Pressure Test Inda Standard Test IST 80.4

A Hydrodrostatic pressure test was performed on the treated polypropylene to test resistance to water penetration when a column of water was placed on the surface. The treated polypropylene was sandwiched between two pieces of plastic with a 2" circular hole in both. The upper piece was attached to a graduated column. Water was introduced through in inlet just over the PP material at a rate that did not allow for a vortex to form. A mirror was positioned below the apparatus and the water was added to the column. The height of the water was recorded once drops of water formed and released from the bottom of the apparatus. The data is shown in the table below. For formulations 13 and 14 no buildup occurred and the water immediately penetrated and began to flow through the polypropylene.

|  | Water Height |
| --- | --- |
| Example Formulation 11 | 1.3 cm |
| Example Formulation 12 | 1.3 cm |
| Example Formulation 13 | Instant |
| Example Formulation 14 | Instant |
| Untreated | 1.0 cm |

Migration

The effect of migration of was examined for the treated polypropylene diaper coverstock. Migration of the hydrophilic coating to adjoining untreated polypropylene is highly undesirable. Dry migration will result in leaks in the final product. The following procedure was used to examine the resistance to migration of the coated polypropylene. Untreated 100% spunbonded SMS (Spunbonded/Meltblown/Spunbonded) polypropylene webs were placed beneath and above 100% spunbonded polypropylene nonwoven web treated with either example formulations 13 or 14. A weight (0.5 lb./in$^2$) was placed on the nonwovens for 1 week at 50° C. to simulate storage and all layers evaluated for hydrophilicity (AATCC Test Method 79-1995). The desired result is to have the top and bottom layers remain hydrophobic and the treated nonwoven to remain hydrophilic. Any change in hydrophilicity of either the top or bottom layer of polypropylene is considered migration. The test was terminated at 300 sec per measurement.

| Middle Layer Treatment | Sheet Location | Strike Through Time |
| --- | --- | --- |
| Example Formulation 13 | Top | >300 sec |
| Example Formulation 13 | Middle | 32 |
| Example Formulation 13 | Bottom | >300 sec |
| Example Formulation 14 | Top | >300 sec |
| Example Formulation 14 | Middle | 11 |
| Example Formulation 14 | Bottom | >300 sec |
| Untreated | Untreated | >300 sec |

No migration was found when either hydrophilic treatment was used. For comparison the process was repeated with a non-curing commercial diaper coverstock treatment. The top and bottom layers exhibited a strike through time of 90-100 seconds. Clearly the hydrophilic treatment migrated from the treated PP to the non-treated PP.

Textile Applications

| Formulations | | | | | | |
| --- | --- | --- | --- | --- | --- | --- |
|  | Example Formulation 15 | Example Formulation 16 | Example Formulation 17 | Example Formulation 18 | Example Formulation 19 | Example Formulation 20 |
| Example O | 0.5% | — | — | — | — | — |
| Example P | — | 0.5% | — | — | — | — |
| Example R | — | — | 0.5% | — | — | — |
| Example L | — | — | — | 0.5% | — | — |
| Example D | — | — | — | — | 0.5% | — |
| Example S | — | — | — | — | — | 0.5% |
| Water | 99.5% | 99.5% | 99.5% | 99.5% | 99.5% | 99.5% |

The synthetic example O, P, R or L was combined with deionized water in a beaker, stirred with an overhead stirrer then acidified to pH 5 with acetic acid.

Formulation and Preparation Procedure for Making a Microemulsion of Control Formulation 2

A 20% microemulsion of Magnasoft Derma NT was made by the addition of 25.0 grams of a commercial polysilicone quat (Momentive Performance Materials) into a disposable beaker to 10.5 grams of TDA-6 and 1.8 grams of TDA-12 (both surfactants made by Ethox). The mixture was stirred using a mechanical stirrer, at moderate speed (~600 rpm) for 5 minutes. Separately a solution of 62.0 grams of deionized water, 0.4 grams of acetic acid, and 0.3 grams of sodium acetate was combined in an addition funnel. The water, acetic acid, and sodium acetate solution was added dropwise over 30 minutes. After the final addition the emulsion was stirrer for an additional 10 minutes.

For treatment in the Pad Bath a dilution of the 20% microemulsion was required. A mechanical stirrer was used and deionized water was added with moderate stirring (~600 rpm) until all the material has been evenly dispersed at an actives concentration of 0.5%.

Treatment by Pad Bath

The diluted treatments (0.5% actives, 150 g) were poured into a disposable beaker. A piece of untreated fabric was weighed and the mass was recorded. The fabric was immersed in the treating solution for 30 seconds or until completely wet. The saturated fabric was passed through a Werner Mathis padder fitted with 4.5" rubber rollers (roller speed—6 M/min, roller pressure—0.5 bar). The fabric was reweighed and the roller pressure was adjusted until 100% wet pick up was achieved. Immediately following the treatment the swatch was placed in a fabric oven at 130° C. for 5 minutes to dry the sample.

Fabric Conditioning

Prior to any physical evaluation of the treated and untreated fabrics, the swatches were placed in an environmental chamber set at 21° C. and 65% RH for a minimum of 24 hours.

Wet Out

The ability of the treatment to increase (hydrophobicity) or decrease (hydrophilicity) the time required for a drop of water to penetrate the surface of the fabric. This test was performed in accordance with the AATCC Test Method 79-1992. A piece of treated or untreated cotton knit fabric was secured in a 6" embroidery ring. Care was taken as to not stretch the fabric but the fabric was taut and free of folds or wrinkles. A drop of deionized water was applied onto the fabric via a dropper and a timer was started. The timer was stopped when the drop of water completely penetrated the fabric and was record in seconds. The process was repeated 6 times at different positions for each fabric. The value reported is the average of these readings, shown in the table below. The test was terminated at 600 seconds. A value of 600 seconds indicates that the drop never penetrated the surface of the fabric.

| Trial | Example Formulation 5 | Example Formulation 16 | Example Formulation 17 | Example Formulation 18 | Control Formulation 2 | Untreated |
| --- | --- | --- | --- | --- | --- | --- |
| 1 | 600 | 80 | 4 | 10 | 10 | 34 |
| 2 | 600 | 21 | 4 | 12 | 10 | 35 |
| 3 | 600 | 74 | 5 | 14 | 12 | 32 |
| 4 | 600 | 32 | 5 | 11 | 12 | 44 |
| 5 | 600 | 145 | 3 | 18 | 12 | 45 |
| 6 | 600 | 92 | 4 | 20 | 13 | 49 |
| Average | 600 | 74 | 4.2 | 14.2 | 11.5 | 39.8 |

The test was repeated for the hydrophobic treatment example formulation 15. Shown in the table are the results when cotton knit fabric is treated and washed. After 1, 3, 5, 10, and 20 washes the fabric was tested for wet out. The fabric remained highly hydrophobic even after 20 washes. The wash/dry procedure is described in the durability section below.

|  | Number of Wash Cycles | | | | |
|---|---|---|---|---|---|
| Trial | 1 | 3 | 5 | 10 | 20 |
| 1 | 600 | 600 | 600 | 410 | 125 |
| 2 | 600 | 600 | 600 | 420 | 118 |
| 3 | 600 | 600 | 600 | 335 | 92 |
| 4 | 600 | 600 | 600 | 480 | 130 |
| 5 | 600 | 600 | 600 | 551 | 95 |
| 6 | 600 | 600 | 600 | 458 | 116 |
| Average | 600 | 600 | 600 | 442.3 | 112.7 |

Wicking

A wicking test was performed in order to evaluate how well the treatments enhance or deter the wicking of water through the fabric. This test was performed in accordance with the ASTM D-5237 test protocol. A 2"×7" strip of treated or untreated fabric was cut from different sample sheets. One end the fabric was marked with a pencil line ~15 mm from the edge. 2 standard metal paper clips were fastened between this line and the edge of the sample. The other end of the fabric was secured a stand with a large (#100) binder clip. The fabric was immersed up to the pencil line in a beaker of colored water. After 6 minutes the fabric samples were removed from the water and the distance from the pencil line to the final position of the wicked water was measured with a ruler and recorded in millimeters. The procedure was repeated 4 times and the measurement were averaged and given in the table below.

| Trial | Example Formulation 5 | Example Formulation 16 | Example Formulation 19 | Un-treated | Control Formulation 2 |
|---|---|---|---|---|---|
| 1 | 15.39 | 76.07 | 0 | 42 | 73.2 |
| 2 | 15.95 | 74.5 | 0 | 40.7 | 73.3 |
| 3 | 12.86 | 72.37 | 0 | 36.4 | 71.9 |
| 4 | 13.15 | 74.1 | 0 | 43 | 72.8 |
| 5 | 12.54 | 72.85 | 0 | 38.9 | 70.3 |
| 6 | 13.53 | 71.67 | 0 | 39.8 | 71.2 |
| Average | 13.9 | 73.6 | 0 | 40.2 | 72.1 |

Durability (Machine Wash/Dry)

The durability study examined how long the treatment remained on cotton knit fabric after repetitive washing and drying. A treated 11"×11" swatch of fabric was placed in a top loader washing machine. The machine was set to a regular wash cycle for a wash period of 12 minutes with a 19 gallon water fill and a temp of 87° F. The detergent used was 60 grams of AATCC Standard Reference Detergent. Once washed the fabric swatches were dried by placing them in a front loader dryer set on timed dry, high heat for 30 minutes. The process was repeated for the given number of wash/dry cycles as dictated in the table below. The fabric samples were then exposed to a $BF_3$ digestion and the silicone content was measured using a GC. The values reported are the percent silicone the remains after the number of washes. For the hydrophilic treatments

| Cycles | Control Formulation 2 | Example Formulation 19 |
|---|---|---|
| 0 | 100% | 100% |
| 1 | 49% | 89% |
| 3 | 35% | No Data |
| 5 | 31% | 117% |
| 10 | 23% | 78% |
| 20 | No Data | 72% |

The test was repeated with example formulation 19 on a 50/50 polyester cotton blend, Dacron, and Nylon. The treatment was not removed after 20 washes for the polyester/cotton blend. There was a decrease in the silicone content for the treated Dacron and Nylon.

|  | 0 | 1 | 5 | 10 | 20 |
|---|---|---|---|---|---|
| Polyester/Cotton Blend 50/50 | 100% | 77% | 118% | 123% | 114% |
| Dacron | 100% | 20% | 9% | 4% | 1% |
| Nylon | 100% | 19% | 36% | 15% | 22% |

Spray Test

An alternate test for durability was performed. A Spray Test was run according to AATCC test method 22-1989. Treated cotton knit fabric was washed in the same manner as described in the Durability section above for 1, 3, 5, 10 and 20 wash/dry cycles. The fabric was secured a 6" embroidery ring. Care was taken so that the fabric did not stretch but it was taut and free of folds or wrinkles. The assembly was placed on the spray test apparatus that consisted of stand holding a jig set at a 45° angle positioned below a large funnel and showerhead. 250 mL of deionized water was poured through the funnel and showerhead onto the test specimen. The specimen/ring was removed and visually rated 0-100 by comparing its appearance to the spray test rating standard. The control sample was an untreated piece of cotton knit. The results are shown in the table below. The high numbers of 121-113 indicate that the surface remains hydrophobic even after 20 washes.

| Wash Cycles | Control Formulation 2 | Example Formulation 19 | Untreated |
|---|---|---|---|
| 0 | 75 | 100 | 0 |
| 1 | 50 | 100 | 0 |
| 3 | 10 | 95 | 0 |
| 5 | 0 | 90 | 0 |
| 10 | 0 | 80 | 0 |
| 20 | 0 | 80 | 0 |

Hand (Soft/Bulk/Slick)

A panel of 5 people was designated to determine the softness and bulkiness that the treatment imparts to cotton knit fabric. The test panels were asked to rate the softness of the fabric from 1 to 10. An untreated swatch of fabric was used to indicate a 1. A high value indicates a very soft and pleasant feel. Most of the formulations tested performed well against the untreated control.

| Treatment | Rating |
|---|---|
| Untreated | 1 |
| Control Formulation 2 | 7.7 |
| Example Formulation 18 | 1 |
| Example Formulation 20 | 7.3 |
| Example Formulation 15 | 6.4 |
| Example Formulation 19 | 6.9 |

The foregoing examples are merely illustrative of the invention, serving to illustrate only some of the features of the present invention. The appended claims are intended to claim the invention as broadly as it has been conceived and the examples herein presented are illustrative of selected embodiments from a manifold of all possible embodiments. Accordingly it is Applicants' intention that the appended claims are not to be limited by the choice of examples utilized to illustrate features of the present invention. As used in the claims, the word "comprises" and its grammatical variants logically also subtend and include phrases of varying and differing extent such as for example, but not limited thereto, "consisting essentially of" and "consisting of." Where necessary, ranges have been supplied; those ranges are inclusive of all sub-ranges there between. Such ranges may be viewed as a Markush group or a collection of Markush groups consisting of differing pairwise numerical limitations which group or groups is or are fully delimited by its lower and upper bounds, increasing in a regular fashion numerically from lower bounds to upper bounds. It is to be expected that variations in these ranges will suggest themselves to a practitioner having ordinary skill in the art and where not already dedicated to the public, those variations should where possible be construed to be covered by the appended claims. It is also anticipated that advances in science and technology will make equivalents and substitutions possible that are not now contemplated by reason of the imprecision of language and these variations should also be construed where possible to be covered by the appended claims. All United States patents (and patent applications) referenced herein are herewith and hereby specifically incorporated by reference in their entirety as though set forth in full.

The invention claimed is:

1. A textile treated with a composition comprising the reaction product of
   a) an oxirane or oxetane compound comprising at least two oxirane or oxetane groups; and
   b) an amino silane having the formula:

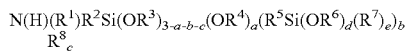

with $R^1$ is chosen from the group consisting of H or a monovalent hydrocarbon radical containing one to 20 carbon atoms;
   $R^2$ is selected from a group consisting of a divalent linear or branched hydrocarbon radical consisting of 1-60 carbons;
   $R^4$ is a hydrocarbon radical that contains 3 to 200 carbon atoms;
   $R^5$ is selected from a group consisting of oxygen or a divalent linear or branched hydrocarbon radical consisting of 1-60 carbons;
   $R^3$, $R^6$, $R^7$, and $R^8$ and are each independently selected from the group of monovalent linear or branched hydrocarbon radicals having from 1 to 200 carbon atoms;
   a positive number and has a value ranging from 0 to 3;
   the subscripts a, and c are zero and b is equal to 3;
   the subscripts d and e are zero or positive and have a value ranging from 0 to 3 subject to the limitation that (d+e) is equal to 3, wherein said textile has an enhanced response to water.

2. The composition of claim 1 where the oxirane or oxetane compound is selected from the group consisting of siloxanes, hydrocarbons and polyethers.

3. The composition of claim 2 where the oxirane or oxetane compound is a siloxane having the formula:

$$M_j M^E_h M^{PE}_i M^H_j D_k D^E_l D^{PE}_m D^H_n T_o T^E_p T^{PE}_q T^H_r Q_s$$

with $M = R^9 R^{10} R^{11} SiO_{1/2}$;
$M^H = R^{12} R^{13} H SiO_{1/2}$;
$M^{PE} = R^{12} R^{13}(-CH_2CH(R^{14})(R^{15})_t O(R^{16})_u (C_2H_4O)_v (C_3H_6O)_w (C_4H_8O)_x R^{17}) SiO_{1/2}$;
$M^E = R^{12} R^{13}(R^E) SiO_{1/2}$
$D = R^{18} R^{19} SiO_{2/2}$; and
$D^H = R^{20} H SiO_{2/2}$
$D^{PE} = R^{20}(-CH_2CH(R^{14})(R^{15})_t O(R^{16})_u (C_2H_4O)_v (C_3H_6O)_w (C_4H_8O)_x R^{17}) SiO_{2/2}$
$D^E = R^{20} R^E SiO_{2/2}$;
$T = R^{21} SiO_{3/2}$;
$T^H = H SiO_{3/2}$;
$T^{PE} = (-CH_2CH(R^{14})(R^{15})_t O(R^{16})_u (C_2H_4O)_v (C_3H_6O)_w (C_4H_8O)_x R^{17}) SiO_{3/2}$;
$T^E = R^E SiO_{3/2}$; and
$Q = SiO_{4/2}$;

where $R^9$, $R^{10}$, $R^{11}$, $R^{12}$, $R^{13}$, $R^{18}$, $R^{19}$, $R^{20}$, and $R^{21}$ are each independently selected from the group of monovalent hydrocarbon radicals having from 1 to 60 carbon atoms;

$R^{14}$ is H or a 1 to 6 carbon atom alkyl group; $R^{15}$ is a divalent alkyl radical of 1 to 6 carbons; $R^{16}$ is selected from the group of divalent radicals consisting of $-C_2H_4O-$, $-C_3H_6O-$, and $-C_4H_8O-$; $R^{17}$ is selected from the group consisting of H, monofunctional hydrocarbon radicals of 1 to 6 carbons, and acetyl;

$R^E$ is independently a monovalent hydrocarbon radical containing one or more oxirane or oxetane moieties having from one to sixty carbon atoms;

the subscript f may be zero or positive subject to the limitation that when the subscript f is zero, h must be positive;

the subscript h is zero or positive subject to the limitations that when h is zero, the subscript f is positive, and that the sum of the subscripts h, l and p is positive;

the subscript k is zero or positive and has a value ranging from about 0 to about 1,000;

the subscript l is zero or positive and has a value ranging from about 0 to about 400 subject to the limitation that the sum of the subscripts h, l and p is positive;

the subscript o is zero or positive and has a value ranging from 0 to about 50;

the subscript p is zero or positive and has a value ranging from 0 to about 30 subject to the limitation that the sum of the subscripts h, l and p is positive;

the subscript s is zero or positive and has a value ranging from 0 to about 20;

the subscript i is zero or positive and has a value ranging from 0 to about 20;

the subscript m is zero or positive and has a value ranging from 0 to about 200;

the subscript q is zero or positive and has a value ranging from 0 to about 30;

the subscript j is zero or positive and has a value ranging from 0 to about 2;

the subscript n is zero or positive and has a value ranging from 0 to about 20;

the subscript r is zero or positive and has a value ranging from 0 to about 30;

the subscript t is zero or one;

the subscript u is zero or one;

the subscript v is zero or positive and has a value ranging from 0 to about 100 subject to the limitation that (v+w+x)>0;

the subscript w is zero or positive and has a value ranging from 0 to about 100 subject to the limitation that (v+w+x)>0;

the subscript x is zero or positive and has a value ranging from 0 to about 100 subject to the limitation that (v+w+x)>0.

4. The reaction product of claim 3 further comprising the reaction product of the aminosilane and a compound having the formula:

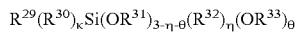

where $R^{29}$ is a monovalent hydrocarbon radical containing one or more oxirane or oxetane moieties having from 3 to 12 carbon atoms;

$R^{30}$ is a divalent hydrocarbon radical consisting of 1-60 carbons and the subscript κ has a value of zero or 1; $R^{31}$ and $R^{32}$ are independently selected from the group of monovalent linear or branched hydrocarbon radicals having from 1 to 60 carbon atoms;

the subscript η is zero or positive and has a value ranging from 0 to 3;

the subscript θ is greater than 0 and less than or equal to 3, subject to the limitation that 3-η-θ is greater than or equal to zero;

$R^{33}$ is a hydrocarbon radical that contains 3 to 200 carbon atoms.

5. The reaction product of claim 3 wherein
$R^1$ has from one to ten carbon atoms;
$R^2$ has from one to ten carbon atoms;
$R^4$ has from three to ten carbon atoms;
$R^3$, $R^6$, $R^7$, and $R^8$ each independently have from one to twenty carbon atoms;
$R^9$, $R^{10}$, $R^{11}$, $R^{12}$, $R^{13}$, $R^{18}$, $R^{19}$, $R^{20}$, and $R^{21}$ each independently have from one to four carbon atoms;
the subscripts f, l, m, n, o, p, q, r, each independently range from 0 to 200;
the subscript k ranges from 0-500;
the subscripts v, w, and x each independently range from 0 to 50.

6. The reaction product of claim 3 wherein
$R^1$ has from one to five carbon atoms;
$R^2$ has from two to eight carbon atoms;
$R^4$ has from three to eight carbon atoms;
$R^3$, $R^6$, $R^7$, and $R^8$ each independently have from one to fifteen carbon atoms;
$R^9$, $R^{10}$, $R^{11}$, $R^{12}$, $R^{13}$, $R^{18}$, $R^{19}$, $R^{20}$, and $R^{21}$ each independently have from one to three carbon atoms;
the subscripts f, l, m, n, o, p, q, r, each independently range from 0 to 100;
the subscript k ranges from 5-250;
the subscripts v, w, and x each independently range from 0 to 35.

7. The reaction product of claim 3 wherein
$R^1$ is hydrogen;
$R^2$ has from two to five carbon atoms;
$R^4$ has from three to five carbon atoms;
$R^3$, $R^6$, $R^7$, and $R^8$ each independently have from two to eight carbon atoms;

$R^9$, $R^{10}$, $R^{11}$, $R^{12}$, $R^{13}$, $R^{18}$, $R^{19}$, $R^{20}$, and $R^{21}$ each independently methyl;
the subscripts f, l, m, n, o, p, q, r, each independently range from 0 to 50;
the subscript k ranges from 5 to 150;
the subscripts v, w, and x each independently range from 0 to 25.

8. The reaction product of claim 4 wherein
$R^1$ has from one to ten carbon atoms;
$R^2$ has from one to ten carbon atoms;
$R^4$ has from three to ten carbon atoms;
$R^3$, $R^6$, $R^7$, and $R^8$ each independently have from one to twenty carbon atoms;
$R^9$, $R^{10}$, $R^{11}$, $R^{12}$, $R^{13}$, $R^{18}$, $R^{19}$, $R^{20}$, and $R^{21}$ each independently have from one to four carbon atoms;
the subscripts f, l, m, n, o, p, q, r, each independently range from 0 to 200;
the subscript k ranges from 0-500;
the subscripts v, w, and x each independently range from 0 to 50;
$R^{31}$ and $^{32}$ each independently have from one to ten carbon atoms and $R^{33}$ has from three to one hundred carbon atoms.

9. Method of treating a textile, comprising the steps of
(i) applying to the textile, a composition comprising the reaction product of
c) an oxirane or oxetane compound comprising at least two oxirane or oxetane groups wherein the oxirane or oxetane compound is selected from the group consisting of siloxanes, hydrocarbons and polyethers; and
d) an amino silane having the formula:

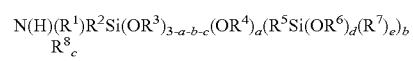

with
$R^1$ is chosen from the group consisting of H or a monovalent hydrocarbon radical containing one to 20 carbon atoms;
$R^2$ is selected from a group consisting of a divalent linear or branched hydrocarbon radical consisting of 1-60 carbons;
$R^4$ is a hydrocarbon radical that contains 3 to 200 carbon atoms;
$R^5$ is selected from a group consisting of oxygen or a divalent linear or branched hydrocarbon radical consisting of 1-60 carbons;
$R^3$, $R^6$, $R^7$, and $R^8$ and are each independently selected from the group of monovalent linear or branched hydrocarbon radicals having from 1 to 200 carbon atoms;
the subscripts a, and c are zero, and b is equal to 3
the subscripts d and e are zero or positive and have a value ranging from 0 to 3 subject to the limitation that (d+e) is equal to 3, wherein said textile has an enhanced response to water, and
(ii) curing.

10. The method of claim 9 where the oxirane or oxetane compound is a siloxane having the formula:

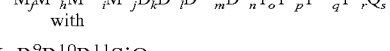
with
$M = R^9 R^{10} R^{11} SiO_{1/2}$;
$M^H = R^{12} R_{13} H SiO_{1/2}$;
$M^{PE} = R^{12} R^{13}(-CH_2 CH(R^{14})(R^{15})_t O(R^{16})_u (C_2 H_4 O)_v (C_3 H_6 O)_w (C_4 H_8 O)_x R^{17}) SiO_{1/2}$;
$M^E = R^{12} R^{13}(R^E) SiO_{1/2}$
$D = R^{18} R^{19} SiO_{2/2}$; and $D^H = R^{20}HSiO_{2/2}$ $D^{PE} = R^{20}(-CH_2CH(R_{14})(R^{15})_tO(R^{16})_u(C_2H_4O)_v(C_3H_6O)_w(C_4H_8O)_xR^{17})SiO_{2/2}$ $D^E = R^{20}R^ESiO_{2/2}$;

$T = R^{21}SiO_{3/2}$;

$T^H = HSiO_{3/2}$;

$T^{PE} = (-CH_2CH(R^{14})(R^{15})_tO(R^{16})_u(C_2H_4O)_v(C_3H_6O)_w(C_4H_8O)_xR^{17})SiO_{3/2}$;

$T^E = R^ESiO_{3/2}$; and $Q = SiO_{4/2}$;

where $R^9$, $R^{10}$, $R^{11}$, $R^{12}$, $R^{13}$, $R^{18}$, $R^{19}$, $R^{20}$, and $R^{21}$ are each independently selected from the group of monovalent hydrocarbon radicals having from 1 to 60 carbon atoms;

$R^{14}$ is H or a 1 to 6 carbon atom alkyl group; $R^{15}$ is a divalent alkyl radical of 1 to 6 carbons; $R^{16}$ is selected from the group of divalent radicals consisting of $-C_2H_4O-$, $-C_3H_6O-$, and $-C_4H_8O-$; $R^{17}$ is selected from the group consisting of H, monofunctional hydrocarbon radicals of 1 to 6 carbons, and acetyl;

$R^E$ is independently a monovalent hydrocarbon radical containing one or more oxirane or oxetane moieties having from one to sixty carbon atoms;

the subscript f may be zero or positive subject to the limitation that when the subscript f is zero, h must be positive;

the subscript h is zero or positive subject to the limitations that when h is zero, the subscript f is positive, and that the sum of the subscripts h, l and p is positive;

the subscript k is zero or positive and has a value ranging from about 0 to about 1,000;

the subscript l is zero or positive and has a value ranging from about 0 to about 400 subject to the limitation that the sum of the subscripts h, l and p is positive;

the subscript o is zero or positive and has a value ranging from 0 to about 50;

the subscript p is zero or positive and has a value ranging from 0 to about 30 subject to the limitation that the sum of the subscripts h, l and p is positive;

the subscript s is zero or positive and has a value ranging from 0 to about 20;

the subscript i is zero or positive and has a value ranging from 0 to about 20;

the subscript m is zero or positive and has a value ranging from 0 to about 200;

the subscript q is zero or positive and has a value ranging from 0 to about 30;

the subscript j is zero or positive and has a value ranging from 0 to about 2;

the subscript n is zero or positive and has a value ranging from 0 to about 20;

the subscript r is zero or positive and has a value ranging from 0 to about 30;

the subscript t is zero or one;

the subscript u is zero or one;

the subscript v is zero or positive and has a value ranging from 0 to about 100 subject to the limitation that (v+w+x)>0;

the subscript w is zero or positive and has a value ranging from 0 to about 100 subject to the limitation that (v+w+x) >0;

the subscript x is zero or positive and has a value ranging from 0 to about 100 subject to the limitation that (v+w +x) >0.

* * * * *